US009931033B2

(12) United States Patent
Kawakami et al.

(10) Patent No.: US 9,931,033 B2
(45) Date of Patent: Apr. 3, 2018

(54) SYSTEM AND METHOD FOR CONTROLLING A FUNDUS IMAGING APPARATUS

(71) Applicant: CANON KABUSHIKI KAISHA, Tokyo (JP)

(72) Inventors: Tomoaki Kawakami, Utsunomiya (JP); Koji Nozato, Rochester, NY (US); Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/179,255

(22) Filed: Jun. 10, 2016

(65) Prior Publication Data

US 2017/0181625 A1 Jun. 29, 2017

Related U.S. Application Data

(60) Provisional application No. 62/271,608, filed on Dec. 28, 2015.

(51) Int. Cl.
*A61B 3/14* (2006.01)
*A61B 3/00* (2006.01)
*A61B 3/12* (2006.01)
*A61B 3/10* (2006.01)
*G02B 27/00* (2006.01)

(52) U.S. Cl.
CPC .......... *A61B 3/1225* (2013.01); *A61B 3/0025* (2013.01); *A61B 3/0041* (2013.01); *A61B 3/102* (2013.01); *A61B 3/1025* (2013.01); *A61B 3/14* (2013.01); *G02B 27/0068* (2013.01)

(58) Field of Classification Search
USPC ................................................. 351/200–246
See application file for complete search history.

(56) References Cited

U.S. PATENT DOCUMENTS

| 5,663,781 A * | 9/1997 | Wilms ............... A61B 3/1025 351/206 |
| 7,535,991 B2 | 5/2009 | Gertner |
| 7,648,242 B2 | 1/2010 | Ferguson et al. |
| 7,758,189 B2 | 7/2010 | Hammer et al. |
| 8,488,895 B2 | 7/2013 | Muller et al. |
| 8,820,931 B2 | 9/2014 | Walsh et al. |

(Continued)

FOREIGN PATENT DOCUMENTS

EP 2517617 B1 11/2014

OTHER PUBLICATIONS

Jie Zhang, Qiang Yang, Kenichi Saito, Koji Nozato, David R. Williams, Ethan A. Rossi, An Adaptive Optics Imaging System Designed for Clinical Use, Biomedical Optics Express, Jun. 1, 2015, 6(6):2120-2137, The Optical Society, Washington DC, 2015.

(Continued)

*Primary Examiner* — Mohammed Hasan
(74) *Attorney, Agent, or Firm* — Canon U.S.A., Inc. IP Division

(57) ABSTRACT

A system, method, medium, controller, or ophthalmoscope for imaging a fundus of a subject. Estimating a first illumination center position for an illumination beam relative to a center position of a pupil of the subject. The first illumination center position may be offset from the center position of the pupil. Sending instructions to an ophthalmoscope to shift a center position of the illumination beam to the first illumination center position.

19 Claims, 15 Drawing Sheets

(56) References Cited

U.S. PATENT DOCUMENTS

| | | | |
|---|---|---|---|
| 8,879,813 B1 | 11/2014 | Solanki et al. | |
| 8,899,749 B2 | 12/2014 | Imamura | |
| 2009/0245602 A1* | 10/2009 | Teige | A61B 3/12 |
| | | | 382/128 |
| 2014/0185009 A1 | 7/2014 | Imamura | |
| 2015/0131050 A1* | 5/2015 | Bublitz | A61B 3/12 |
| | | | 351/206 |
| 2015/0297076 A1 | 10/2015 | Cremer et al. | |
| 2016/0227998 A1* | 8/2016 | Schmoll | A61B 3/12 |

OTHER PUBLICATIONS

Austin Roorda, Applications of Adaptive Optics Scanning Laser Ophthalmoscopy, PubMed Central, NIH Public Access Author Manuscript, Apr. 1, 2011, PMCID: PMC2911957, pp. 1-17, National Center for Biotechnology Information, U.S. National Library of Medicine, Bethesda MD, 2011.

Gerald Westheimer, Directional Sensitivity of the Retina: 75 Years of Stiles—Crawford Effect, Proceedings of the Royal Society B: Biological Sciences, Dec. 28, 2008, 275(1653)2777-2786, The Royal Society, London, GB, 2008.

* cited by examiner

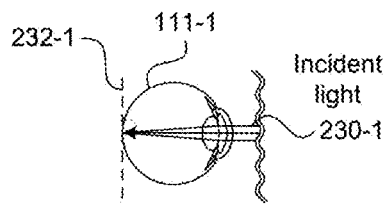
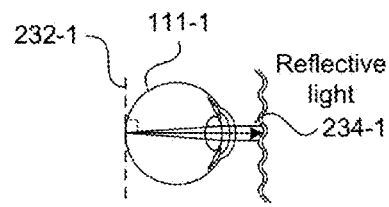
FIG. 2A  FIG. 2B
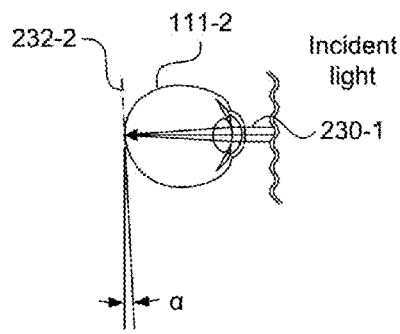
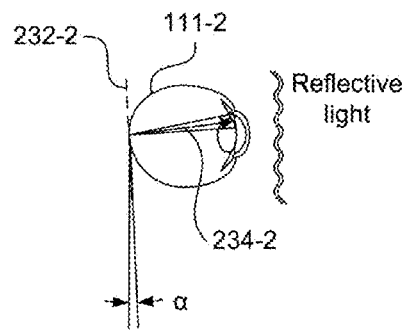
FIG. 2C  FIG. 2D
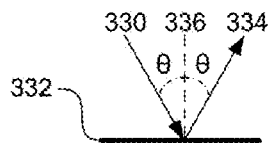
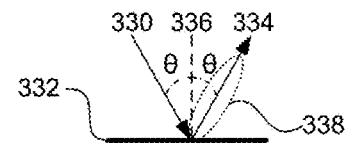
FIG. 3A  FIG. 3B
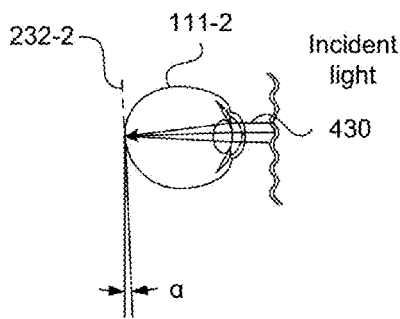
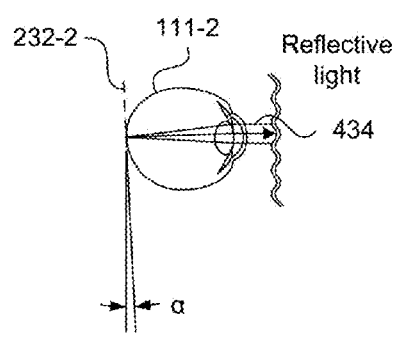
FIG. 4A  FIG. 4B

β < 0

β = 0

β > 0

SYSTEM AND METHOD FOR CONTROLLING A FUNDUS IMAGING APPARATUS

CROSS-REFERENCE TO RELATED APPLICATIONS

This application claims the benefit of U.S. Provisional Application No. 62/271,608, filed Dec. 28, 2015. U.S. Provisional Application No. 62/271,608 is hereby incorporated by reference in its entirety.

BACKGROUND

Field of Art

The present disclosure relates to an ophthalmic apparatus, a system and a method for controlling an ophthalmic apparatus.

Description of the Related Art

An ophthalmoscope is an apparatus for gathering information about the interior portion of an eye (fundus). A simple direct view ophthalmoscope is a handheld device used by an optician to directly view the fundus which may include light source, aperture, and one or more lenses. An electronic ophthalmoscope use one or more sensors to obtain fundus images. These fundus images are then displayed to the optician with a display device. A high resolution ophthalmoscope may use lasers to obtain high resolution fundus images. A high resolution ophthalmoscope may also include adaptive optics to obtain even higher resolution fundus images. The adaptive optics can be used to compensate for the static and dynamic distortions introduced by the eye being examined. Examples of ophthalmoscopes include but are not limited to: ophthalmic image pickup apparatuses; fundus imaging systems; scanning laser ophthalmoscopes (SLO); adaptive optics scanning laser ophthalmoscope (AO-SLO); optical coherence tomographs (OCT); that utilize the interference of low coherence light; and adaptive optics optical coherence tomographs (AO-SLO). These ophthalmoscopes are important tools for the study of the human fundus in both normal and diseased eyes.

In AO-SLO and AO-OCT the adaptive optics (AO) are an optical correction system that measures the aberration of the eye and corrects for the measured aberration. The AO-SLO and AO-OCT may measure the wavefront of the eye using a Shack-Hartmann wavefront sensor system. A deformable mirror or a spatial-phase modulator is then driven to correct for the measured wavefront, and an image of the fundus is acquired, thus allowing AO-SLO and AO-OCT to acquire high-resolution images.

One of the challenges for gathering information about the fundus is that the reflectance at the retina (a part of the fundus) is very small (around 0.1%). Also, the amount of light that can be used to measure the fundus is limited by eye safety concerns. Thus, it can be difficult for a SLO to detect reflective light. One goal of an ophthalmoscope is to effectively light up the fundus so that the ophthalmoscope can gather a lot of reflective light. Providing enough illumination, by effectively lighting up the fundus, is the key to detecting enough light from the fundus whether it is reflective light and/or fluorescence light. If the illumination light enters the pupil off-center then a part of the illumination is kicked backed by the pupil and illumination light actually entering the eye is decreased. A result of this kick back is that reflective light from the fundus and light detected by the SLO decreases. Thus, in the prior art it was generally desirable that the SLO apparatus is set so that illumination light went through the center of pupil.

The inventors have determined that in some cases, where the prior art method of co-centering the center of the illumination beam with the center of the subject's pupil actually makes it harder to get a good fundus image. For example if the surface or interface being imaged has a tilt that is large then the reflected light may be directed away from the center of the pupil and the pupil will block some or all of the reflected light.

SUMMARY

One aspect of an embodiment may be a method for imaging a fundus of a subject. The method may comprise estimating a first illumination center position for an illumination beam relative to a center position of a pupil of the subject. Wherein, the first illumination center position may be offset from the center position of the pupil. The method may further comprise sending instructions to an ophthalmoscope to shift a center position of the illumination beam to the first illumination center position.

In an aspect of another embodiment, shifting the center position of the illumination beam to the first illumination center position and away from the center of the pupil, may improve an image quality of an image of the fundus obtained by the ophthalmoscope.

In an aspect of another embodiment the image quality of the image of the fundus may be estimated based on one or more properties of the image of the fundus including: a contrast ratio; a brightness, and a spatial frequency.

In an aspect of another embodiment estimation of the first illumination center position may be based on one or more images selected from: an OCT image; an anterior ocular segment image; a SLO image; a first image that includes information about a surface tilt of a surface of an area of the fundus being imaged; and a second image that includes information about a sub-surface tilt of a sub-surface feature below the area of the fundus being imaged.

In an aspect of another embodiment may further comprise displaying results of an aberration measurement along with direction and magnitude the first illumination center position relative to the center of the pupil.

In an aspect of another embodiment estimation of the first illumination center position may comprise identifying an interface of a feature on or below an area of the fundus being imaged. It may further comprise estimating a tilt of the interface. It also may comprise estimating a first incidence angle at which the illumination beam irradiates the interface so as to minimize how much light reflected by the interface with the tilt is blocked by the pupil. It also may comprise estimating the first illumination center position such that the illumination beam is incident on the area of the fundus being imaged at the first incidence angle based on optical properties of the subject.

In an aspect of another embodiment the optical properties of the subject may be estimated based on an eyeglass prescription of the subject.

In an aspect of another embodiment the interface may be a line between the photoreceptor interior segment and the photoreceptor outer segment measured within an OCT image.

In an aspect of another embodiment the ophthalmoscope may be an adaptive optics scanning laser ophthalmoscope having an aberration measurement optical system to measure aberration of the subject and obtain fundus images.

In an aspect of another embodiment the ophthalmoscope may shift the center position, with one or more of: a movable mirror, a movable lens, a moveable window, and a phase shifter.

In an aspect of another embodiment the ophthalmoscope may maintain the center position of the illumination beam at the first illumination center position offset from the center position of the pupil during scanning. During scanning the illumination beam may be scanned across an area of the fundus.

In an aspect of another embodiment shifting the center position of the illumination beam may reduce the amount of light which is incident on the fundus and increase the quality of the image obtained from the fundus.

In an aspect of another embodiment estimating the first illumination center position may further comprise sending instructions to the ophthalmoscope to shift the center position of the illumination beam to a test illumination center position. It also may comprise obtaining a test image from the ophthalmoscope. It also comprises obtaining a quality metric based on the test image. It also may comprise comparing the quality metric to a first threshold. It also comprises in the case where the quality metric does not meet the first threshold performing a first sub-test method. The first sub-test method may comprise sending instructions to the ophthalmoscope to shift the center position of the illumination beam to a new test illumination center position. The first sub-test method may also comprise obtaining a new test image from the ophthalmoscope. The first sub-test method may comprise obtaining a new quality metric based on the new test image. The first sub-test method may comprise comparing the new quality metric to the first threshold. The first sub-test method may comprise in the case where the new quality metric does meet the first threshold setting the new test illumination center position as the first illumination center position. The first sub-test method may comprise in the case where the new quality metric does not meet the first threshold repeating the first sub-test method with a different new test illumination center position. Estimating the first illumination center position may further comprise in the case where the quality metric does meet the first threshold, setting the test illumination center position as the first illumination center position.

In an aspect of another embodiment imaging the fundus may comprise obtaining a plurality of images. Each image among the plurality of images may be representative of a particular area of the fundus. Each particular area of the fundus may be associated with a particular first illumination center position. Each image received from the ophthalmoscope may be obtained with the center position of the illumination beam shifted to the particular first illumination center position associated with the particular area of the fundus being imaged.

In an aspect of another embodiment each of the particular first illumination centers may be stored as a plurality of first illumination centers. Each of the plurality of first illumination centers may be associated with a particular area of the subject.

In an aspect of another embodiment a non-transitory computer-readable medium may be encoded with instructions for performing a method for imaging a fundus of a subject. The method may comprise instructions for estimating a first illumination center position for an illumination beam relative to a center position of a pupil of the subject. The first illumination center position may be offset from the center position of the pupil. The method may comprise instructions for sending instructions to an ophthalmoscope to shift a center position of the illumination beam to the first illumination center position.

In an aspect of another embodiment may be a controller configured to control an ophthalmoscope for imaging a fundus of a subject. The controller may comprise: a processor; and a memory. The processor may estimate a first illumination center position for an illumination beam relative to a center position of a pupil of the subject. The first illumination center position may be offset from the center position of the pupil. The processor may send instructions to the ophthalmoscope to shift a center position of the illumination beam to the first illumination center position.

In an aspect of another embodiment the controller may further comprise the ophthalmoscope.

In an aspect of another embodiment, the ophthalmoscope may comprise an optical component configured to shift the center position of the illumination beam to the first illumination center position.

BRIEF DESCRIPTION OF THE DRAWINGS

The accompanying drawings, which are incorporated in and constitute a part of the specification, illustrate exemplary embodiments.

FIGS. 2A-D are illustrations of light incident on and reflected from a subject.

FIGS. 3A-B are illustrations of light incident on, reflected from, and scattered from a subject.

FIGS. 4A-D are illustrations of light incident on and reflected from a subject.

DESCRIPTION OF THE EMBODIMENTS

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following which is used to inspect an eye as described below may also be used to inspect other objects including but not limited to skin, and internal organs.

Ophthalmoscope

Figure 1A:
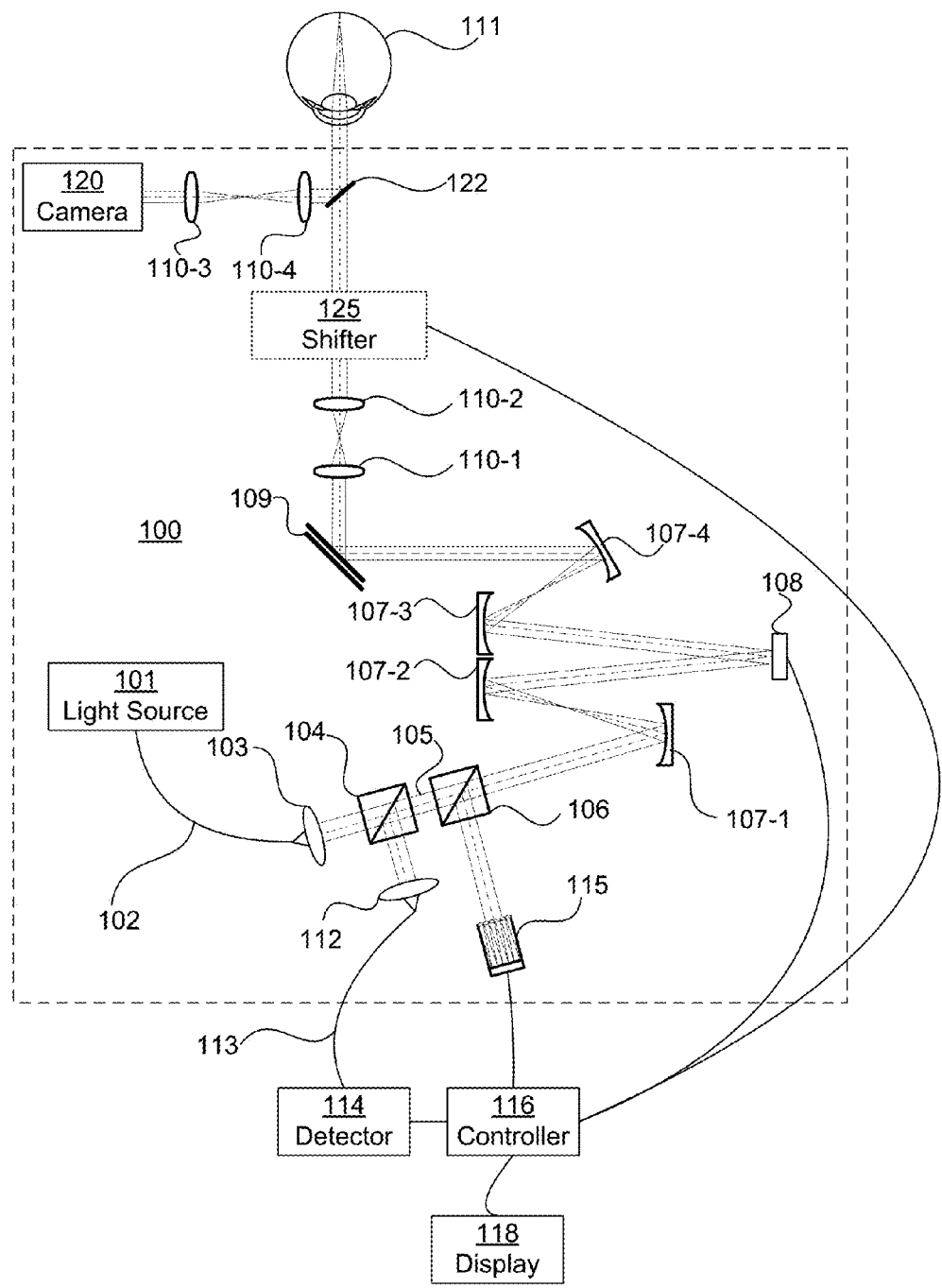
FIG. 1A is a generalized illustration of an apparatus in which an embodiment may be implemented.

A first embodiment is described with reference to an ophthalmoscope 100 such as fundus image photographing apparatus illustrated in FIG. 1A. Embodiments are directed towards systems, methods, non-transitory computer readable medium, and software which are used in connection with an imaging system such as an ophthalmoscope 100. FIG. 1A is an illustration of an exemplary ophthalmoscope 100. An ophthalmoscope 100 is a system or apparatus for obtaining information about an interior portion of the eye 111 (e.g., the fundus or retina).

An exemplary embodiment may be a scanning ophthalmoscope. A scanning ophthalmoscope scans a spot across the eye 111 with a scanner 109. The spot may be a spot of light from a light source 101 that is scanned across the eye 111.

In an exemplary embodiment 100, the spot of light is produced by a light source 101. The light source 101 may be incorporated into the ophthalmoscope 100; alternatively, the ophthalmoscope 100 may include an input for receiving the light source 101. The input for the light source 101 may be a fiber optic input 102 or a free space input (not shown). The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare perceived by a person being inspected and to maintain imaging resolution.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration, the light source 101 is polarized and the single-mode optical fiber 102 is polarization maintaining fiber. In another configuration, the polarization adjusting member may be placed after the collimator 103. Alternatively, the polarization adjusting member may be replaced with a polarizer. In an alternative embodiment, the irradiated light may be unpolarized, depolarized, or the polarization may be uncontrolled.

The measuring light 105 radiated from the collimator 103 passes through a light division portion 104 including a beam splitter. An exemplary embodiment includes an adaptive optical system.

The adaptive optical system may include a light division portion 106, a wavefront sensor 115, wavefront adjustment device 108, and reflective mirrors 107-1, 107-2, 107-3, and 107-4 for guiding the measuring light 105 to and from those components. The reflective mirrors 107-1 to 107-4 are provided to guide the measuring light 105 to and from the pupil of an eye 111, the wavefront sensor 115, and the wavefront adjustment device 108. The reflective mirrors may be replaced with suitable optics, such as lenses and/or apertures. Likewise, the lenses may be replaced with mirrors. The wavefront sensor 115 and the wavefront adjustment device 108 may be in an optically conjugate relationship. A beam splitter may be used as the light division portion 106. The wavefront sensor 115 may be a Shack-Hartmann sensor or other type of sensor that gathers information that is representative on the spatial nature of the wavefront of light coming from the subject 111. Other examples of types of sensors that provide information about the shape of a wavefront include but are not limited to: a pyramid wavefront sensor; common path interferometer; Foucault knife-edge tester; a multilateral shearing interferometer; a Ronchi tester; and a Shearing Interferometer.

The measuring light 105 passing through the light division portion 106 is reflected by the reflective mirrors 107-1 and 107-2 so as to enter the wavefront adjustment device 108. The measuring light 105 is reflected by the wavefront adjustment device 108 and is further reflected by the reflective mirrors 107-3 and 107-4.

The wavefront adjustment device 108 may be a transmissive device or a reflective device. The wavefront adjustment device 108 may be an addressable spatial light phase modulator that allows relative phases across a beam coming into the wavefront adjustment device 108 to be adjusted such that relative phases across the beam coming out of the wavefront adjustment device 108 are adjustable. In an exemplary embodiment, one or two spatial phase modulators each including a liquid crystal element is used as the wavefront adjustment device 108. The liquid crystal element may modulate a phase of only a specific polarized component. In which case, two liquid crystal elements may be employed to modulate substantially orthogonal polarized components of the measuring light 105. In an alternative embodiment, the wavefront adjustment device 108 is a deformable mirror.

The measuring light 105 reflected off mirror 107-4 is two-dimensionally scanned by a scanning optical system 109. The scanning optical system 109 may a system including a first scanner 109-1 (not shown) and a second scanner 109-2 (not shown). The scanning optical system may also include additional optical components (mirrors and/or lenses) for guiding light between the scanners. The first scanner 109-1 rotates around the first axis, while the second scanner 109-2 rotates around a second axis. The first axis is substantially orthogonal to the second axis. Substantially in the context of the present disclosure means within the alignment and measurement tolerances of the system. The scanning optical system 109 may include one or more additional scanners 109-3 (not shown) which are used for steering the scanning area to different parts of the fundus.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single tip-tilt mirror that is rotated around the first axis and around the second axis that is substantially orthogonal to the first axis. An exemplary embodiment may also use non-mechanical beam steering techniques, such as phase steering.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency. There may be additional optical components, such as lenses, mirrors, apertures, and etc. between the scanners 109-1, 109-2, and other optical components. These additional optical components may be arranged such that the light is focused onto the scanners, in a manner that is optically conjugate with all of or one or more of the subject 111, the wavefront adjustment device 108, the wavefront sensor 115, and a detector 114.

The measuring light 105 scanned by the scanning optical system 109 is radiated onto the eye 111 through eyepieces 110-1 and 110-2. The measuring light radiated to the eye 111 is reflected, scattered, or absorbed by the fundus 111. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

The ophthalmoscope 100 may also include a camera 120. The camera 120 may include a sensor for capturing exterior images of the eye 111 or images of the anterior segment of the eye 111. The camera 120 may also be used to capture video images of the eye 111. The camera 120 may be used to detect visible light reflected from the eye 111. The visible light may come from a visible light source (not shown) or ambient light. The camera 120 may be used along with a dichroic filter 122. The dichroic filter 122 may reflect visible light from the eye 111 that is detected by the camera 120 while letting measurement light 105 pass straight through. Light reflected from the dichroic filter 122 may be guided to the camera 122 by lenses 110-3 and 110-4. Lenses 110-3 and 110-4 may be replaced with one or more curved mirrors. The apparatus 100 may include an optional shifter 125 that may be used for shifting a center position of the illumination beam relative to a center position of the pupil of the subject 111. The shifter may include one or more optical components such as a movable mirror, a movable lens, a moveable window, and a phase shifter. The shifter 125 may be located between the scanning mirror 109 and the subject 111. The shifter 125 may be incorporated into a wide field tracking mirror. in one embodiment the shifter may be implanted by rotating a parallel plate window placed in the path of the illumination beam. Wherein the window has an anti-reflection coating (AR) on both sides of the window.

Light which is produced by reflection, fluorescence, and/or scattering by a fundus of the eye 111 then travels in the reverse direction along the same path as the incident measurement light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor may be employed or a method of obtaining the wavefront by reverse calculation from the spot images may also be employed.

In FIG. 1A, when the reflected light passes through the light division portion 106, a part thereof is reflected on the light division portion 104 and is guided to a light intensity sensor 114 (detector) through a collimator 112 and an optical fiber 113. The light intensity sensor 114 converts the light into an electrical signal. The electrical signal is processed by a controller 116 or other suitable processing device into an image of the subject and the image is displayed on a display 118.

The wavefront sensor 115 is also connected to the controller 116. The received wavefront is transferred to the controller 116. The wavefront adjustment device 108 is also connected to the controller 116 and performs modulation as instructed by the controller 116. The controller 116 calculates a modulation amount (correction amount) to obtain a wavefront having less aberration based on the wavefront obtained by a measuring result of the wavefront sensor 115, and instructs the wavefront adjustment device 108 to perform the modulation according to the modulation amount. The wavefront measurement and the instruction to the wavefront adjustment device are repeated and a feedback control loop is maintained so as to obtain a suitable wavefront for obtaining a signal by the detector 114.

In an exemplary embodiment the light division portions 104 and 106 are partially reflective mirrors. In an alternative exemplary embodiment, the light division portions 104 and/or 106 may include fused fiber couplers. In another alternative exemplary embodiment, the light division portions 104 and/or 106 may include dichroic reflectors, in which case a different wavelength of light is used for obtaining an image of the fundus then is used for detecting the spatial phase image that controls the adaptive optics system.

The detector 114 may detect scattering, reflection, or fluorescence associated with the scanning spot. The detection system may make use confocal microscopy techniques in which an aperture associated with the scanning spot is used to increase the resolution and/or contrast of the detection system.

The adaptive optics system described above includes at least the wavefront sensor 115 and the wavefront adjustment device 108 so that the aberration of the subject's eyes can be measured and compensated for. A deformable mirror (DM) or a spatial light phase modulator (SLM) can be used as the wavefront adjustment device 108. Since the typical SLM has a large number of actuators, it can modulate wavefront more precisely than the DM can. A liquid crystal on silicon spatial light modulator (LCOS-SLM) may be used as the wavefront adjustment device 108. The LCOS-SLM 108 can be controlled to provide a precise spatial modulation of the phase of the beam that is used to illuminate the subject.

Controller

Figure 1B:
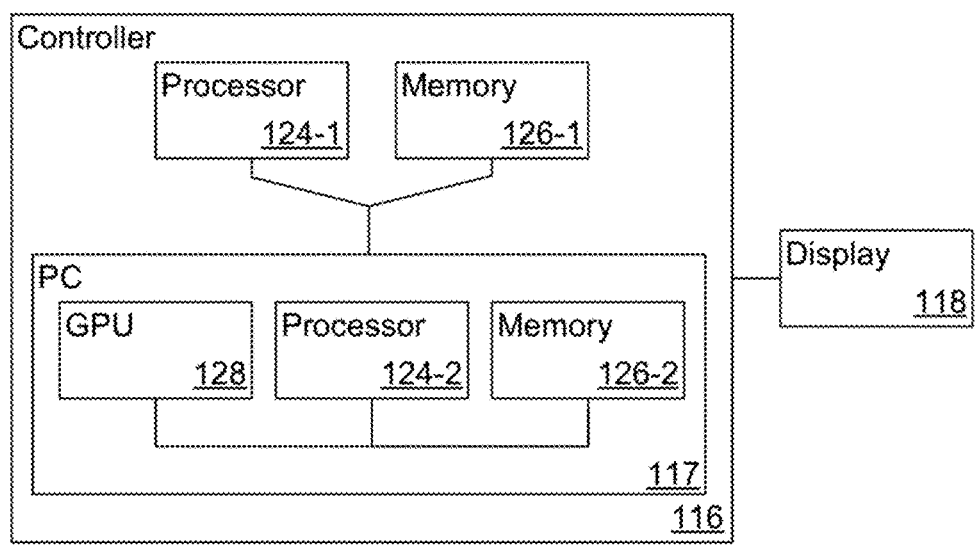
FIG. 1B is an illustration of a controller in which an embodiment may be implemented.

FIG. 1B is an illustration of the controller 116 that may be used in an embodiment. The controller 116 may also include a PC 117. The controller 116 receives input values and outputs control values to and from the ophthalmoscope 100. In an alternative embodiment, the controller may be a part of the ophthalmoscope 100. The controller 116 may be a general purpose computer, a device specifically designed to control the ophthalmoscope or measuring instrument, or a hybrid device that uses some custom electronics along with a general purpose computer 117. The input values and control values may be digital values or analog values. The controller 116 may include an analog to digital converter (ADC) and a digital to analog converter (DAC). The input values may include one more values such as a signal from the wavefront sensor 115, a signal from the detector 114, and one or more values from one or more other sensors. The control values may include control values sent to a wavefront adjustment device 108 and values sent to one or more of the scanners 109-1, 109-2, and 109-3. The control values may include additional values to other components of the instrument.

The controller 116 includes a processor 124-1. The processor 124-1 may be a microprocessor, a CPU, an ASIC, a DSP, and/or a FPGA. The processor 124-1 may refer to one or more processors that act together to obtain a desired result. The controller 116 may include a memory 126-1. The memory 126-1 may store calibration information. The memory 126-1 may also store software for controlling the ophthalmoscope. The memory 126-1 may take the form of a non-transitory computer readable storage medium. The non-transitory computer readable storage medium may include, for example, one or more of a hard disk, a random-access memory (RAM), a read only memory (ROM), a distributed storage system, an optical disk (CD, DVD or Blu-Ray Disc, a flash memory device, a memory card, or the like. The controller 116 may include input devices such as a keyboard, a mouse, a touch screen, knobs, switches, and/or buttons.

The controller 116 may be connected to a computer (PC) 117 via a direct connection, a bus, or via a network. The computer 117 may include input devices such as a keyboard, a mouse, and/or a touch screen. The computer 117 may be connected to a display 118. The results and/or data produced by the ophthalmoscope 100 may be presented to a user via the display 118. The PC 117 may include a processor 124-2, and a memory 126-2. The PC 117 may also include one or more GPUs 128.

Optical Coherence Tomograph (OCT)

Figure 1C:
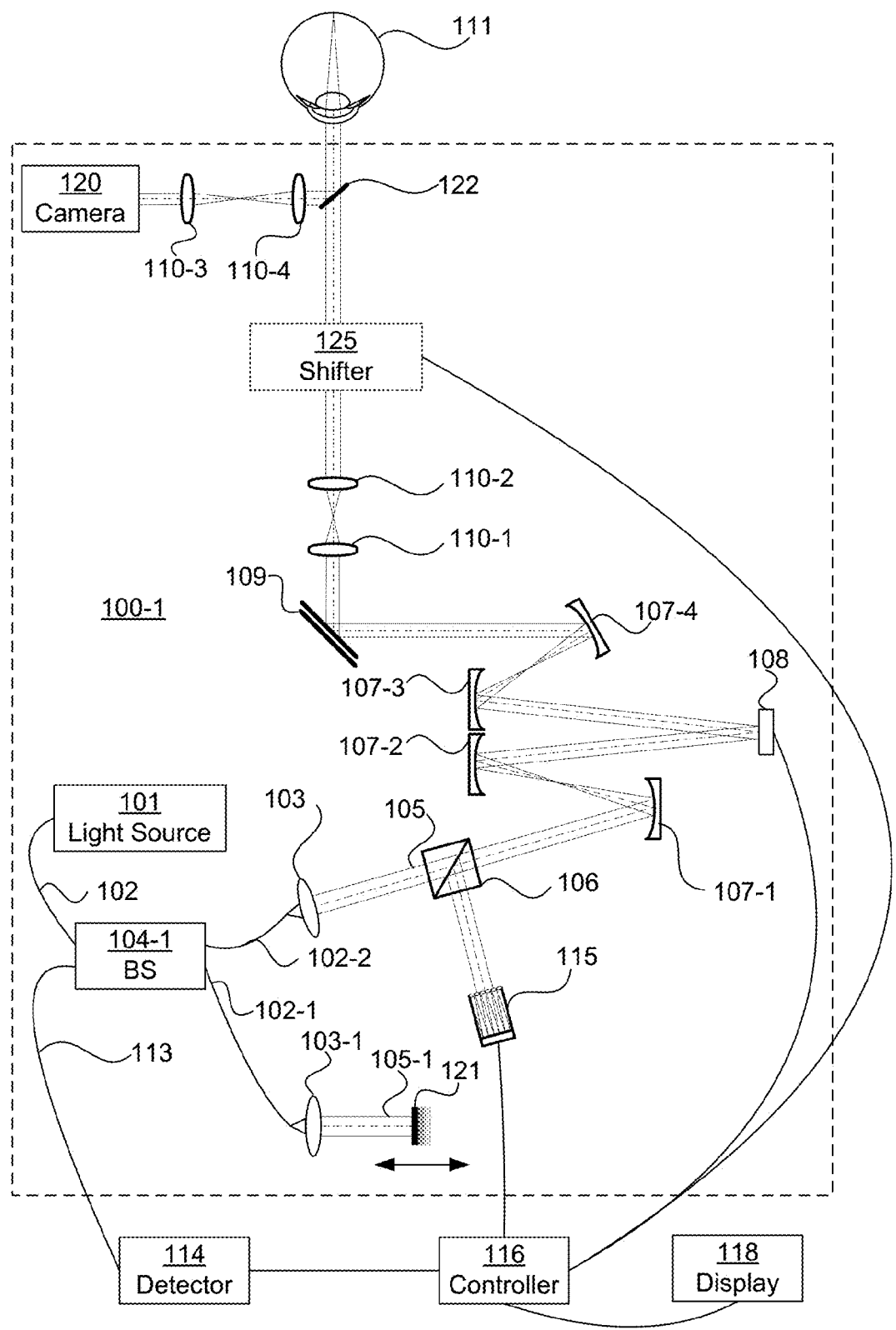
FIG. 1C is a generalized illustration of an apparatus in which an embodiment may be implemented.

FIG. 1C is an illustration of an OCT 100-1 which may be in an embodiment or in combination with an embodiment. The OCT 100-1 is substantially similar to the ophthalmoscope 100. Elements of the ophthalmoscope 100 which are substantially the same as in the OCT will not be described. The OCT may include a light source 101. The light source 101 is low coherence light source. The light source 101 may be fiber coupled. The light from the light source may be sent to a beamsplitter 104-1. The beam splitter 104-1 may send a first portion of the light to a collimator 103 so as to form a measurement beam 105. The beam splitter 104-1 may also send a second portion of the light to second collimator 103-1. The second collimator 103-1 may form a reference beam 105-1. The reference beam 105-1 may be reflected a movable or static mirror 121.

The measurement light 105 is used in substantially the same way as in the ophthalmoscope 100. Light is gathered from the subject 111 and returned back the beamsplitter 104-1. The beamsplitter 104-1 also receives reference light 105-1 reflected by the mirror 121. The beamsplitter 104-1 combines the received reference light 105-1 and the received measurement light 105 and sends the combined light to a detector 114. The detector 144 may detect a light intensity signal, interference fringes, and/or spectral signal. The beamsplitter 104-1 may be a fused fiber coupler and light may be guided between components with fiber optics 102, 102-1, 102-2, and 113. In the alternative the beamsplitter 104-1 may be a free space beam splitter and conventional lenses and/or mirrors may be used to guide the light between the various components.

Eye Shape and the Effect on Reflective Light

FIG. 2A is an illustration of a typical normal eye 111-1. An illumination beam such as from the measurement beam 105 enters they eye 111-1 as incident light 230-1. The crystallin lens of the eye 111-1 focuses the incident light 230-1 onto a portion of the back surface of the fundus. The dashed line 232-1 represents a line perpendicular to a center line of the incident light 230-1. The dashed line 232-1 also represents a plane that is substantially parallel to an interface of the fundus which reflects light back out of the normal eye 111-1 as reflective light 234-1 as illustrated in FIG. 2B. The interface of the fundus may be a surface of the fundus such as the photoreceptor cell, the retinal pigment epithelium or an internal interface of the fundus such as vitreoretinal interface. There is a strong directional dependence in the reflective and scattering of light by asymmetrical components of the eye such as the photoreceptor cells. These interfaces are biological interfaces and are thus rarely planar but on average may be approximated by an effectively locally planar surface. In many cases this approximation is sufficient to produce measureable results.

FIG. 2C is an illustration a second eye 111-2. In this second eye 111-2 a plane 232-2 is substantially parallel to a biological interface that reflects light back from the fundus of the second eye 111-2. In the case illustrated in FIGS. 2C-D the plane 232-2 is not normal to a center line of incident light 230-1 that is co-centered with a center of a pupil of the second eye 111-2. Instead, the plane 232-2 forms an angle $\alpha$ with a plane normal to the center line of the incident light 230-1 as illustrated in FIG. 2C. This causes reflective light 234-2 to be reflected at angle as illustrated in FIG. 2D. Depending on the diameter of the incident beam, the diameter of the pupil, and the angle $\alpha$, the pupil will block a portion of the reflected light 234-2. As the angle $\alpha$ increases then the portion of the light that is blocked by the pupil increases. Also as the difference between the diameter of the incident beam and the diameter of the pupil decreases the portion of the light that is blocked by the pupil increases. The amount of light block by the pupil decreases the amount of light that can be detected by the detector 114.

The inventors have determined that in some cases an optimal position for a center-line of an illumination beam is not co-centered with a center of a pupil. In some cases, when the interface being imaged is tilted it is advantageous to have a center line of an illumination beam be offset from the center of the pupil.

FIGS. 3A-B are illustrations of the directivity of reflected light. Incident light 330 illuminates a planar interface 332 at an incident angle $\theta$ relative to a normal vector 336 of the surface 332. FIG. 3A illustrates a case in which planar interface 332 is a perfect reflector, in which case the reflected light 334 leaves the interface at an opposite angle $\theta$ relative to a normal vector 336. Most Biological tissues are not perfect reflectors and are instead weak scatters. The inventors have found that it is reasonable to assume that the interfaces and surfaces being imaged in the retina are weak scatters and thus the specular reflection of incident light 300 is strongest in the regular reflective direction 334. The scattered light 338 tends to have an intensity distribution which is peaked at the regular reflective direction 334 as illustrated in FIG. 3B.

The applicants have determined that in this case, it is possible to adjust the incidental angle of illumination of the fundus, such that the amount of reflective light increases to a maximum. This is done until we an optimal pupil position through an off axis position of pupil is set.

Figure 4C:
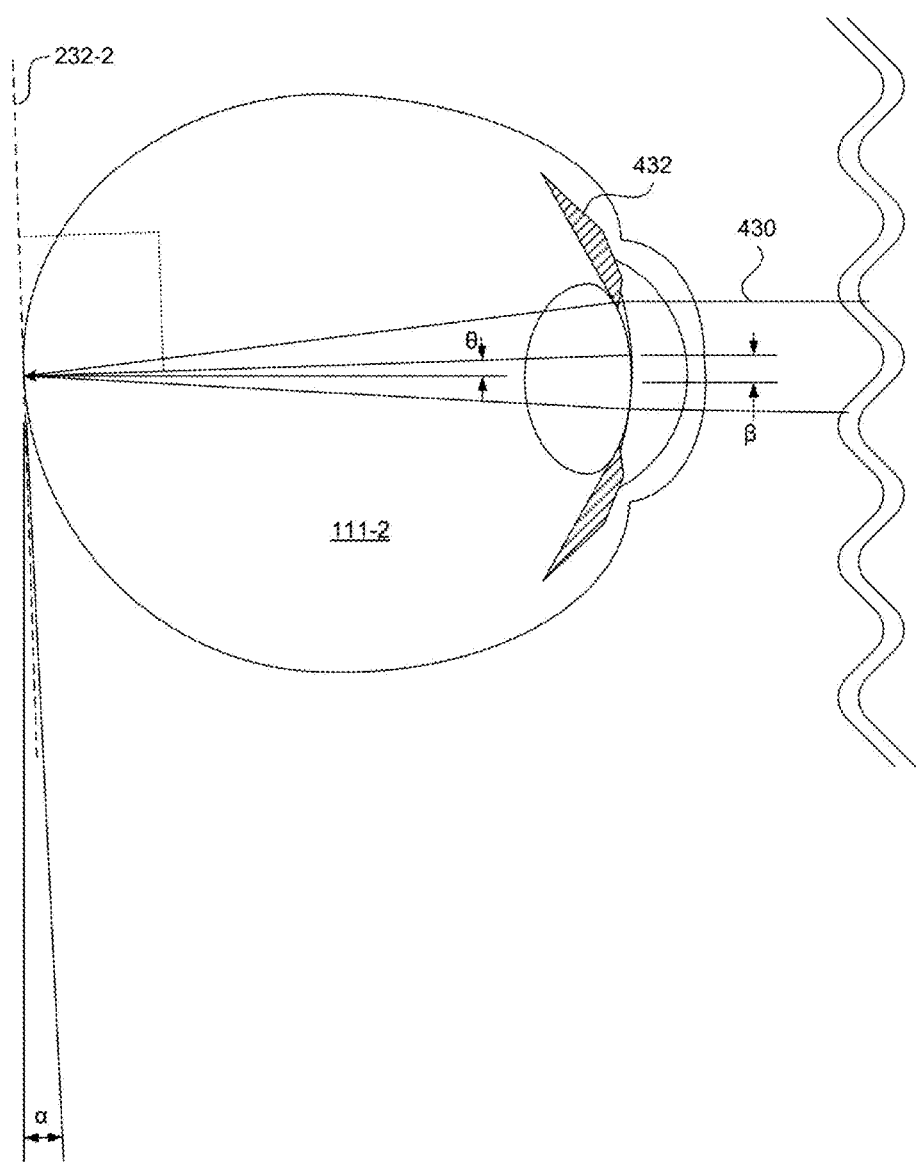

FIGS. 4A-C are illustrations of a case in which the incident beam 430 is offset to compensate for a tilt of a degrees of the plane 232-2 of interest. The incident beam 430 enters the eye 111-2, except in this case it is offset from the pupil center. The lens of the eye 111-2 focuses the incident beam 430 onto the back of the fundus. Incident beam 430 intersects the tilted plane 232-2 at an angle $\theta$. FIG. 4B illustrates how the reflected light 434 (which is reflected back from the tilted plane 232-2) exits the pupil instead of being blocked by the pupil. This is due to the fact that the incident beam 430 intersects the tilted plane and angle at which the incident beam intersects the plane of interest 232-2 is optimized such that the light exits through the pupil. FIG. 4C is an enlarged view of FIG. 4A. In which the offset between the center of the incident beam and a center of the pupil is illustrated as the distance $\beta$. Also shown is how some of the light is blocked by the iris 432 of the eye 111-2.

Example with Results

Figure 5B:
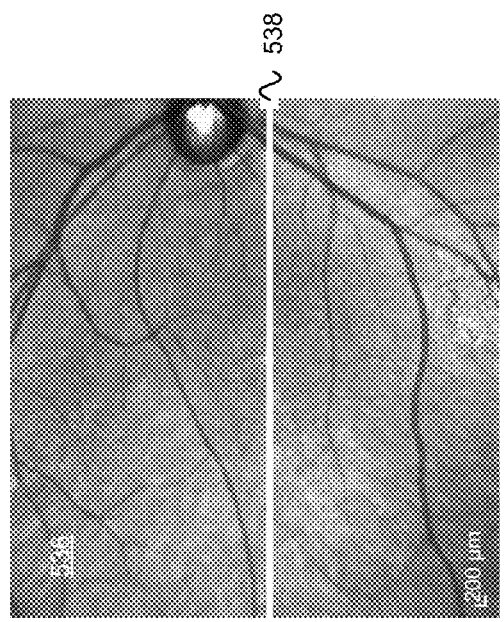
FIGS. 5A-C are illustrations of images obtained from a subject by an embodiment.
Figure 5A:
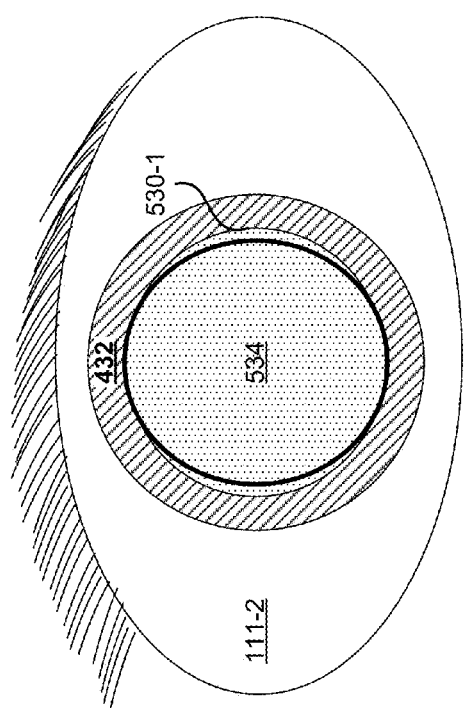

FIGS. 5A-C and 6A-C are illustrations of a subject and data which may be obtained in one embodiment. In one embodiment, we may know the tilt of the fundus or the plane of interest. We may obtain the tilt of the fundus or the plane of interest by referring to an OCT image, anterior ocular segment image, and/or a wide field SLO image. FIG. 5A is an illustration of an exemplary eye 111-2. The eye 111-2 includes an iris 432, which is illustrated as an annular disc. The iris 432 is illustrated with slanted lines to distinguish it from other components of the eye. The eye 111-2 also includes a pupil 534 the edges of which are illustrated as a thick dark line. The eye 111-2 is initially illuminated with an initial incident beam 530-1. A center-line of the initial incident beam 530-1 may be substantially co-centered with a center of the pupil 534. Substantially in the context of the present embodiment is within the measurement tolerance, alignment tolerance, and biological variation of the subject.

Figure 5C:

FIG. 5B is an illustration of a wide field SLO image 536 obtained of the eye 111-2. The line 538 is representative of the position of the OCT image 540 shown in FIG. 5C. As illustrated in FIG. 5C plane of interest is tilted relative to the imaging system at angle α. The tilt α of photoreceptor interior segment outer segment (IS/OS) line can be easily seen in the OCT image 540.

Figure 6B:
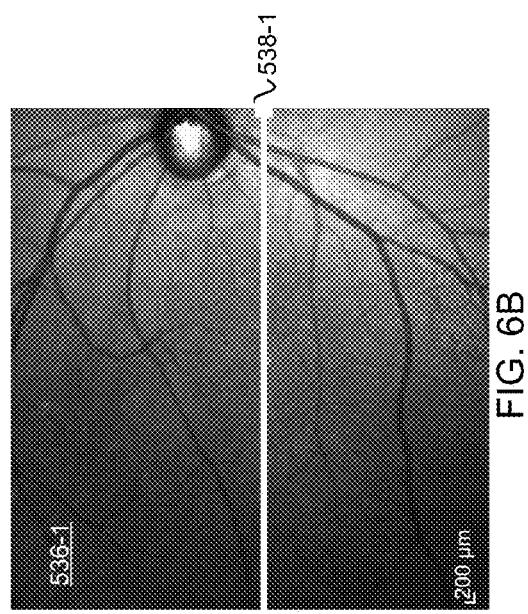
FIGS. 6A-C are illustrations of images obtained from a subject by an embodiment.
Figure 6A:
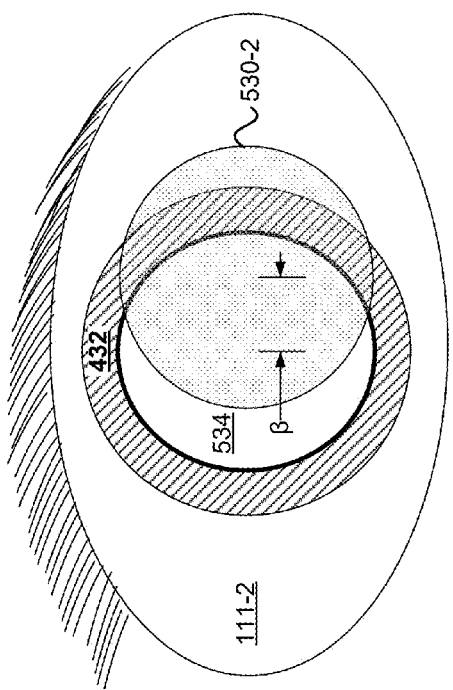

FIG. 6A is an illustration of the same eye 111-2 except now the incident beam 530-2 is offset from the center of the pupil by a distance β. FIG. 6B is an illustration of a wide field SLO image 536-1. The line 538-1 is representative of an intersection of the SLO image 536-1 and an OCT image 540-1. The IS/OS line is tilted at angle $α_{new}$ in the OCT image 540-1 illustrated in FIG. 6C. The angle $α_{new}$ is less than the angle α. Doing so allows the OCT 100-1 to obtain the OCT image 540-1 which is of higher quality then the image 540. A comparison of these two images 540 and 540-1 show that more of the details at and around the IS/OS line are clearer and easier to identify. FIG. 6A is an illustration of an offset position β the measurement beam 105 relative to the pupil 534 of the subject's eye 111. The display 118 may present an image to an operator that is representative of the direction and magnitude the first illumination center position relative to the center of the pupil.

Figure 6C:

By illuminating the subject 111 through the center of the pupil 534 an embodiment can determine a tilt α of a plane of interest such as the IS/OS line in an OCT image 540. When the tilt α of the fundus is large, it may be difficult to determine the tilt α of IS/OS line at the edge of an OCT image 540. In the case in which it is difficult to determine the tilt α, the embodiment may illuminate the fundus at an off axis position β relative to the pupil 534 to the degree that an embodiment can identify the IS/OS line clearly and determine the tilt α as illustrated in FIG. 6C.

A look up table (LUT) may be created to describe the relationship between α and an offset β for a particular subject 111. A LUT may also be created by mapping particular areas of the subject 111 with particular offsets β prior to imaging.

The amount and the direction of tilt α in each image, can be used by an embodiment to predict an optimal offset β pupil illumination position so that the reflective light gathered by the embodiment increases. The prediction may make use of tables of optimal offset β pupil illumination positions which may be estimated beforehand by using the data from images such as (OCT image, anterior ocular segment image, and/or wide field SLO image) of the subject. An embodiment can use this method to increase the amount of reflective light from the retina than would otherwise be obtained without using this method.

The amount of reflective light from the retina may also depend on the orientation of the rods and cones of the retina structure (Ref1: Gerald WESTHEIMER, Directional Sensitivity of the Retina: 75 Years of Stiles—Crawford Effect, Proceedings of the Royal Society B, Sep. 2, 2008, 275 (1653):2777-2786, The Royal Society, London UK, 2008). Ref1 describes how a part of the pipe-shaped visual cell consists of a multilayer film structure, and this film structure causes strong multiple reflections of any incident light. For this reason, it is not only necessary to consider the degree of tilt α of the retina but also the orientation of the visual cell. An embodiment may compensate for this situation by first adjusting the pupil position at the above-mentioned expected most suitable pupil position β based on the estimated tilt β, and then minutely adjusting the pupil position β to a new β that takes into account the orientation of the rods and cones.

Figure 7:
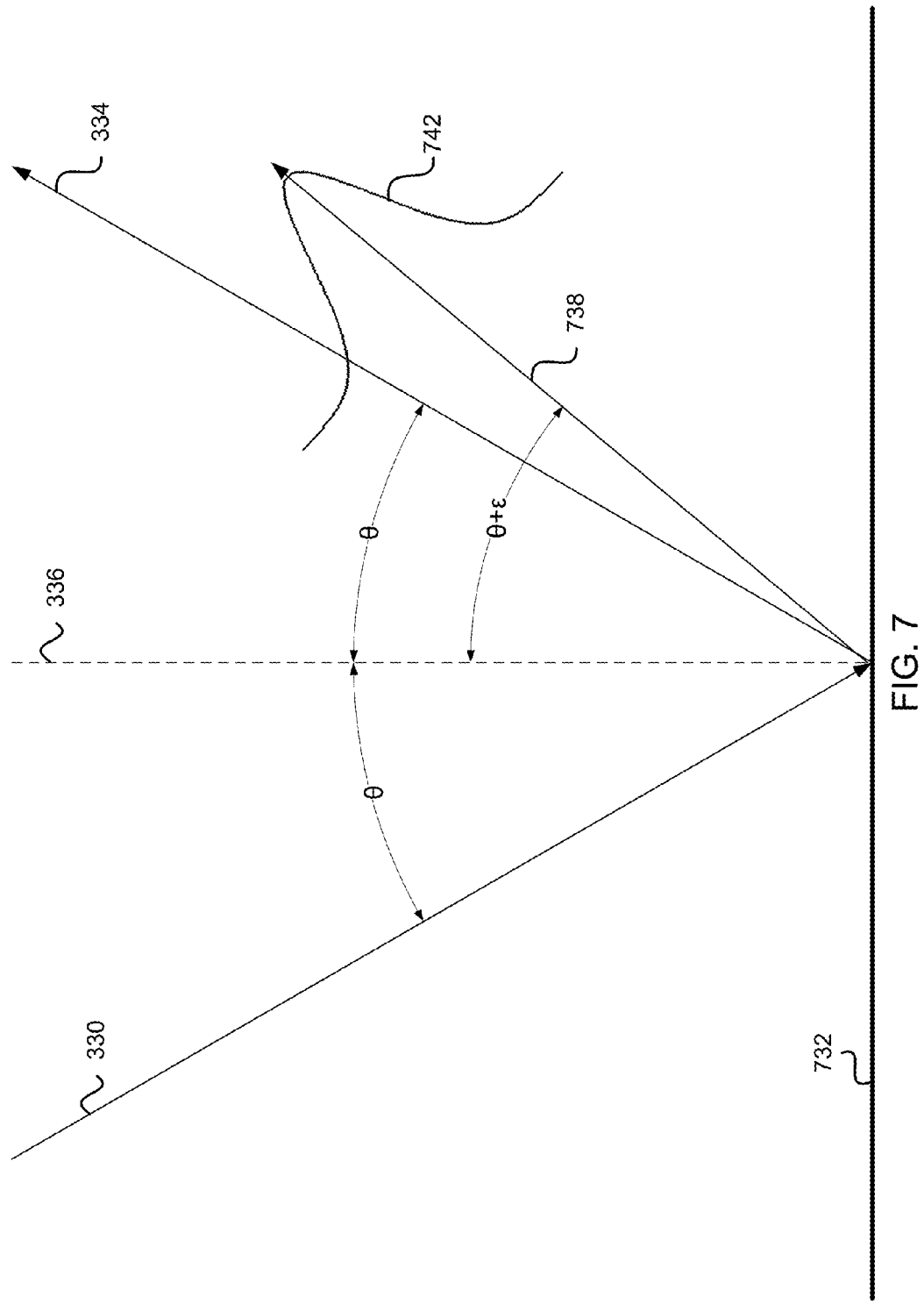
FIG. 7 is an illustration of how light is scattered from a subject in an embodiment.

In other words, the retina is not an ideal reflector and scatters light with an angular dependence as illustrated in FIG. 7. FIG. 7 is an expansion on the concept illustrated in FIG. 3B. The incident light 330 illuminates a planar surface 732 at an incident angle of θ relative to a normal vector 336 of the surface 732. An ideal reflector would reflect light at an opposite angle θ relative to the normal vector 336. Assuming the surface 732 is not an ideal reflector, the incident light is scattered and forms a distribution 742 of light. The peak of this angular dependence may not be centered on the opposite of the incident angle θ as in a mirror but is instead peaked along the direction 738 at the angle θ+ε. In which the angle ε may be a positive or negative angle. An embodiment may adjust the incidence angle θ to find an ideal incidence angle in which the best image may be obtained.

Figure 8C:
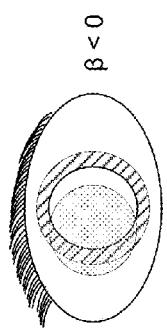
FIGS. 8A-I are illustrations of images obtained from a subject by an embodiment.
Figure 8B:
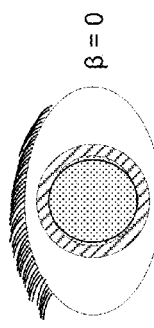
Figure 8A:
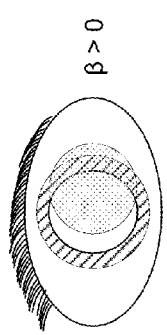

An embodiment may make small changes in the pupil position β so that the obtained images have the largest values of a quality metric. Examples of such a quality metric are image contrast ratio, feature sharpness, and image brightness. FIGS. 8A-I are illustrations of the results of making changings to the pupil position β and the resultant images. FIG. 8B is an illustration of a subject in which the measurement beam is centered on the pupil, such that β is substantially zero. FIG. 8A is an illustration of a subject in which the measurement beam is shifted to the right of the pupil, such that β is greater than zero. FIG. 8C is an illustration of a subject in which the measurement beam is shifted to the left of the pupil, such that β is less than zero.

Figure 8F:
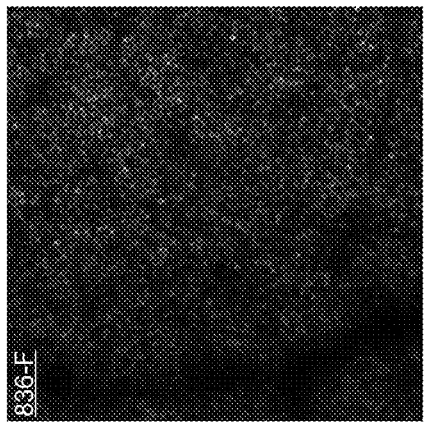
Figure 8E:
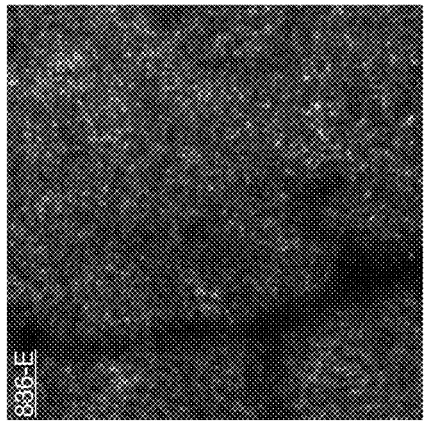
Figure 8D:
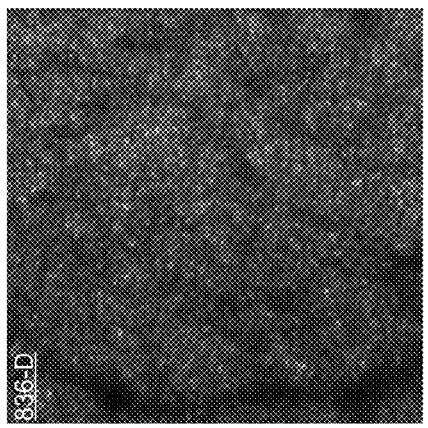

FIG. 8D is an illustration of a photoreceptor mosaic image 836-D that was obtained in which β is greater than zero. FIG. 8E is an illustration of a photoreceptor mosaic image 836-E that was obtained in which β is substantially zero. FIG. 8F is an illustration of a photoreceptor mosaic image 836-F that was obtained in which β is less than zero.

Figure 8I:
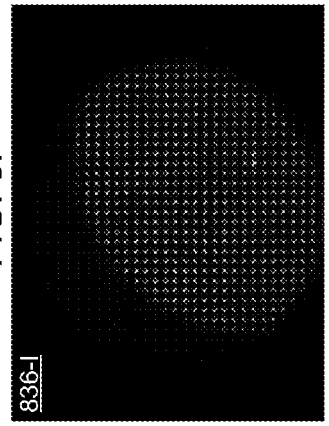
Figure 8H:
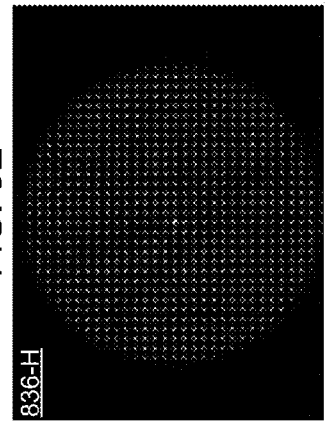
Figure 8G:
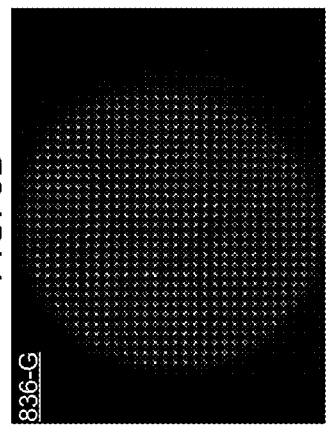

FIG. 8G is an illustration of a Hartmann spot image 836-G that is representative of a shape of a wavefront of light from the subject obtained in which β is greater than zero. FIG. 8H is an illustration of a Hartmann spot image 836-H that is representative of a shape of a wavefront of light from the subject obtained in which β is substantially zero. FIG. 8I is an illustration of a Hartmann spot image 836-I that is representative of a shape of a wavefront of light from the subject obtained in which β is less than zero.

A goal of an embodiment, may be to find and maintain an optimal pupil position β. The optimal pupil position β is determined by the subject's 111 characteristics. For a living subject 111, the eye and pupil will move during imaging.

While this movement occurs the pupil position β should be maintained relative to the moving center of the pupil so as to obtain good quality images. An embodiment may include a pupil position tracking capability. The position of the pupil of the subject 111 may be tracked using the camera 120. In an alternative embodiment, the position of the pupil of the subject 111 may be tracked using a wide field SLO image. In an embodiment, the controller 116 may monitor the pupil position and manipulate the measurement beam's 105 position so as to keep β in the optimal position. In an alternative embodiment, the position of the subject 111 may be manipulated relative to the measurement beam 105.

Fluorescence

An alternative embodiment may also measure fluorescence images using the same method. In the alternative embodiment, the amount of fluorescence light that is collected also increases because illumination efficiency of the incident light increases. This allows the alternative embodiment to acquire a higher quality image using this method.

The light distribution of the fluorescence may be unknown. In an embodiment, the pupil position may be changed such that the contrast ratio is increased. In an embodiment, the pupil position may be changed such that the brightness is increased. In an embodiment, the pupil position may be changed such that a certain spatial frequency in the image is increased. In an embodiment, the pupil position may be changed so as to maximize a fluorescence quality metric based on the fluorescence light image. The fluorescence quality metric may be based on a one or more quality metrics such as contrast ratio, brightness, uniformity, etc.

Scanning Area and Offset

Figure 4D:
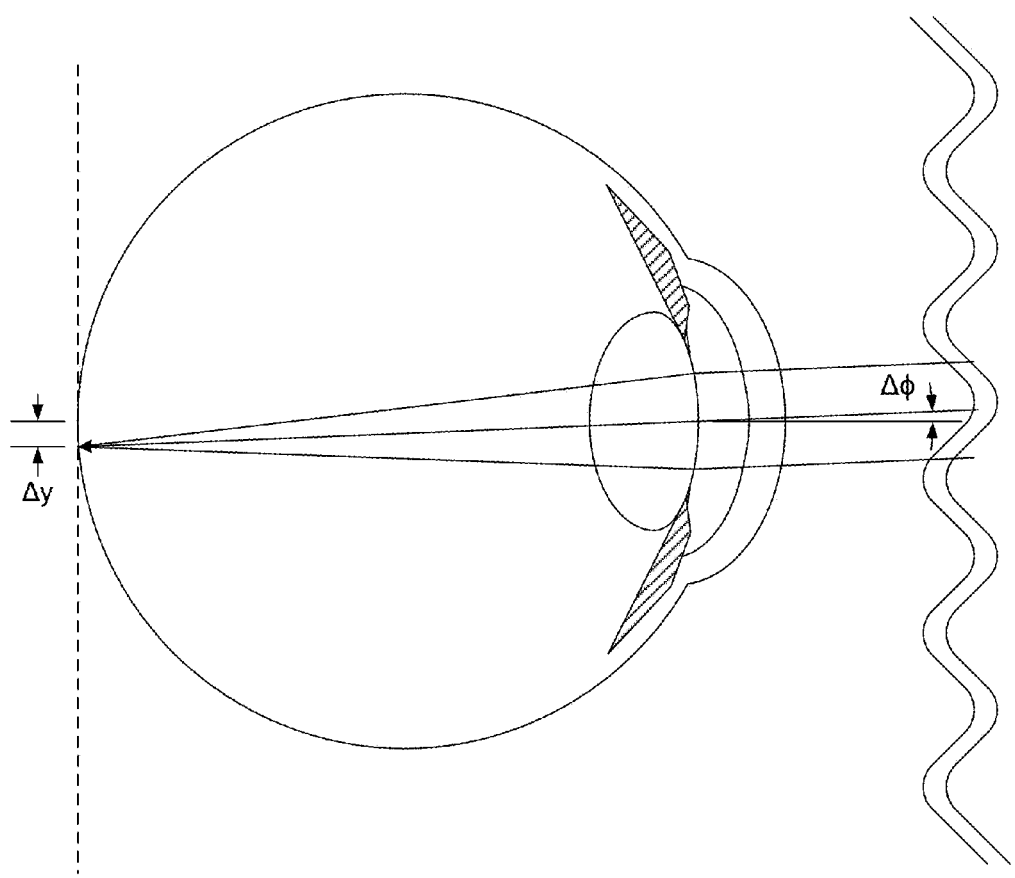

The angle θ at which the center of the scanning beam is incident on the fundus is controlled by shifting the center of the scanning beam 530 by β relative to the center of the pupil 534 and lens of the subject 111 as illustrated in FIG. 4C. The lens of the subject 111 will then tilt the beam in accordance with the shape of the lens. Also an area of the fundus of the subject 111 that is being imaged is controlled by the angle of incidence Δφ of the scanning beam 530 at the pupil 534 which shifts the light beam as it is incident on the fundus by a distance Δy as illustrated in FIG. 4D. A similar change in an orthogonal change of the angle of incidence will shift the incident beam in an orthogonal direction Δx. The tilt of the incident beam at the pupil effects the position at which the scanning beam is incident on the fundus, while the offset of the incident beam at the pupil effects the tilt of the beam at the fundus.

A First Setup Method

Figure 9A:
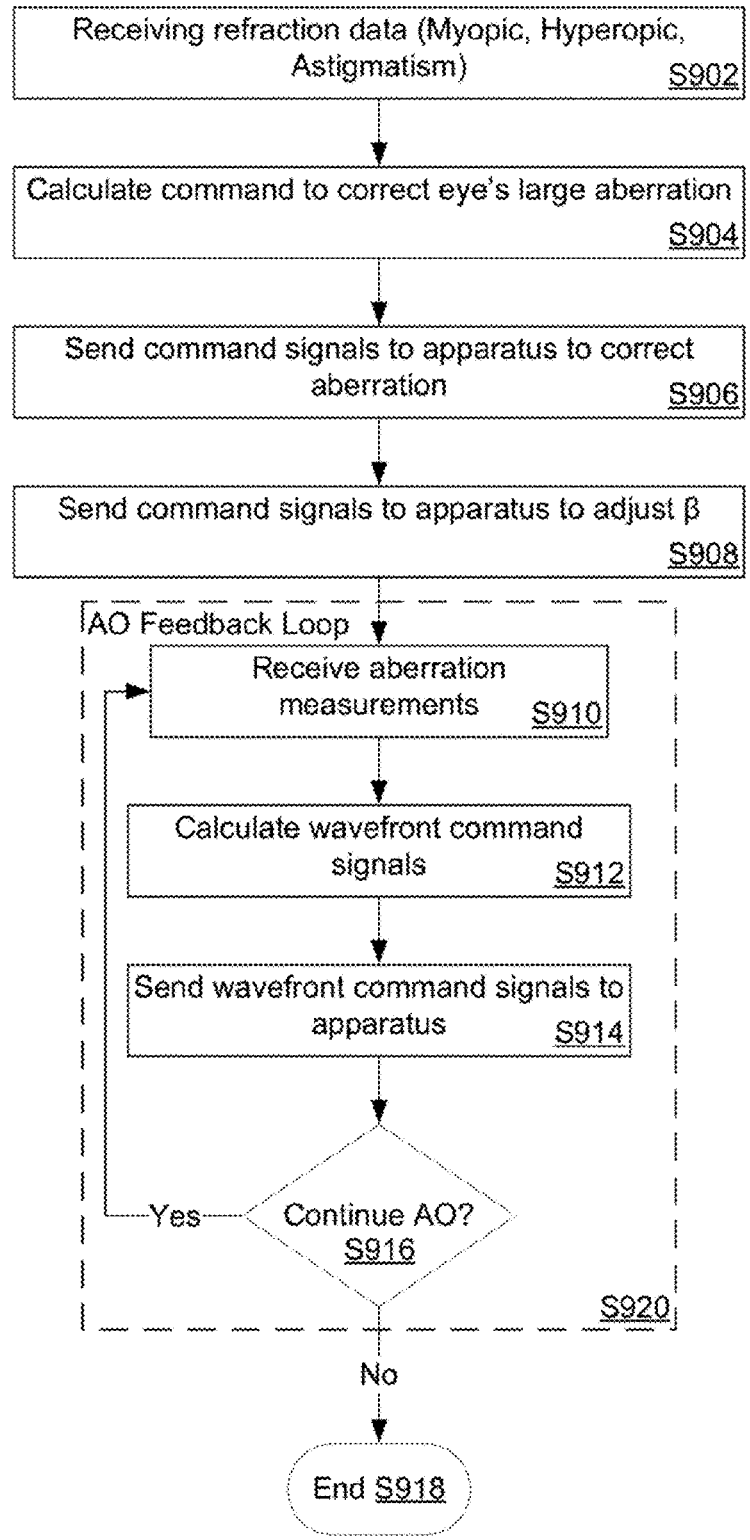
FIGS. 9A-E are illustrations of methods performed by embodiments.

FIG. 9A is an illustration of a method 900-1 of an embodiment. The method 900-1 may be implemented by a controller 116. A non-transitory computer readable medium may be encoded with instructions for performing the method 900-1. The controller 116 may receive instructions for performing the method 900-1 from a server on a local intranet or via a distant server over an internet network link. The method 900-1 may be an imaging setup procedure after which one or more images may be obtained which are then used to evaluate the subject 111.

A first step S902 of the method 900-1 may include the controller 116 receiving refraction data about the subject 111. The refraction data may include eyeglass prescription data, refractive error, and/or general classification of the type of error such as Myopic, Hyperopic, or Astigmatism. The refraction data may be entered by an operator or retrieved by the controller 116 from a server.

A second step S904 of the method 900-1 may include the controller 116 calculating a set of control signals which compensate at least in part for the aberration introduced by the subject 111. The control signals may be calculated using the refraction data to estimate the effect of the refractive error represented by the refraction data on a measurement beam and estimating what optical correction that could be provided by the ophthalmoscope 100 would improve the ability of the ophthalmoscope 100 to gather information about the fundus.

A third step S906 of the method 900-1 may include the controller 116 sending control signals to the ophthalmoscope 100. The control signals may include instructions for the ophthalmoscope 100 to move one or more of the optical elements 110-1, 110-2, and/or other optical elements. Instead of or in addition to moving the optical elements the control signals may also include instructions to adjust the wavefront with the wavefront adjustment device 108.

The method 900-1 may include a fourth step S908 in which the controller 116 sends command signals to apparatus 100 to adjust β. The ophthalmoscope 100 may adjust β by moving one or more of the optical elements including lenses or mirrors. In addition to moving the optical elements, the control signals may also include instructions to adjust the wavefront with the wavefront adjustment device 108. The ophthalmoscope 100 may include specific optical elements that laterally move the measurement beam without changing the incidence angle. Examples of such specific optical elements may include but are not limited to laterally moving one or more mirrors (e.g. first surface mirrors) and/or rotating a transparent window (e.g. glass window with AR coatings).

In one embodiment, β is a scalar value that represents the displacement along one axis. In another embodiment, β is a vector with a magnitude and a direction that represents the amount of displacement and a direction of the displacement. In yet another embodiment β is at least two scalar values which together represent the displacement along at least two orthogonal axes.

The method 900-1 may include a fifth step S910. The fifth step S910 may include the controller receiving aberration data $a_n$, (e.g. structured data, unstructured data, analog signals, digital signals, etc.) from the wavefront sensor 115 of the ophthalmoscope 100 at a temporal index n. The aberration data is an approximate representation of a shape of a wavefront of light that is received by the ophthalmoscope 100 from the subject 111. Alternatively, the controller 116 may use the aberration data to estimate a shape of a wavefront of light that received by the ophthalmoscope 100 from the subject 111. The aberration data $a_n$, includes a plurality of aberration data elements. Each aberration data element representing a local estimation of the shape of a wavefront of light that is received by the ophthalmoscope 100 from the subject 111. The aberration data $a_n$, may take the form of a matrix or a vector.

The method 900-1 may include a sixth step S912. The sixth step S912 may include the controller 116 calculating wavefront command signals $w_n$. The wavefront command signals may include a plurality of wavefront command elements. The wavefront command signals may be calculated based on equation (1) shown below. Equation (1) has been presented as a matrix equation, but other well-known methods of calculating the wavefront command elements may be used.

$$w_n = G a_n + w_{n-1} \qquad (1)$$

The wavefront command signals $w_n$ may be a vector or matrix that represents the command signals that the controller 116 will send to the wavefront adjustment device 108 of the ophthalmoscope 100. Each wavefront command element is representative of an instruction on how to adjust the phase of the wavefront in a local area of the measurement beam. The size and dimension of the wavefront command $w_n$ may not be the same size as the aberration data $a_n$. A gain G is a scalar value or a matrix that is representative of the gain that is applied to aberration data $a_n$ which is then added to the previous value of the wavefront command $w_{n-1}$. The gain G may also transform a vector of aberration data $a_n$ of a first size to a vector of second size of the wavefront command $w_n$.

The method 900-1 may include a seventh step S914. The seventh step S914 may include the controller 116 sending wavefront command signals to the wavefront adjustment device 108 of the ophthalmoscope 100. The wavefront command signals may take the form of specific instructions on how to adjust the phase of specific portions of the measurement beam 105 with the wavefront adjustment device 108. Alternatively, wavefront command signals may take the form of higher order instructions based on the overall shape of the wavefront.

The method 900-1 may include a eighth step S916. The eighth step S916 may include the controller 116 determining whether to continue with the AO feedback loop using steps S910, S912, and S914. The controller 116 may make this determination based upon one or more image quality metrics or changes in relative quality metrics, such as brightness, contrast, uniformity, sharpness, etc. relative to one or more thresholds. The controller 116 may also make this determination based upon input from an operator. If the controller 116 determines that AO feedback should continue then method 900-1 may go back to step S910, thus forming the AO feedback loop S920. If the controller 116 determines that AO feedback should stop, then the method 900-1 may move on to step S918 and the method 900-1 may stop. At this point additional images may be obtained in which the settings for β determined in the method 900-1 is used.

A Second Setup Method

Figure 9B:
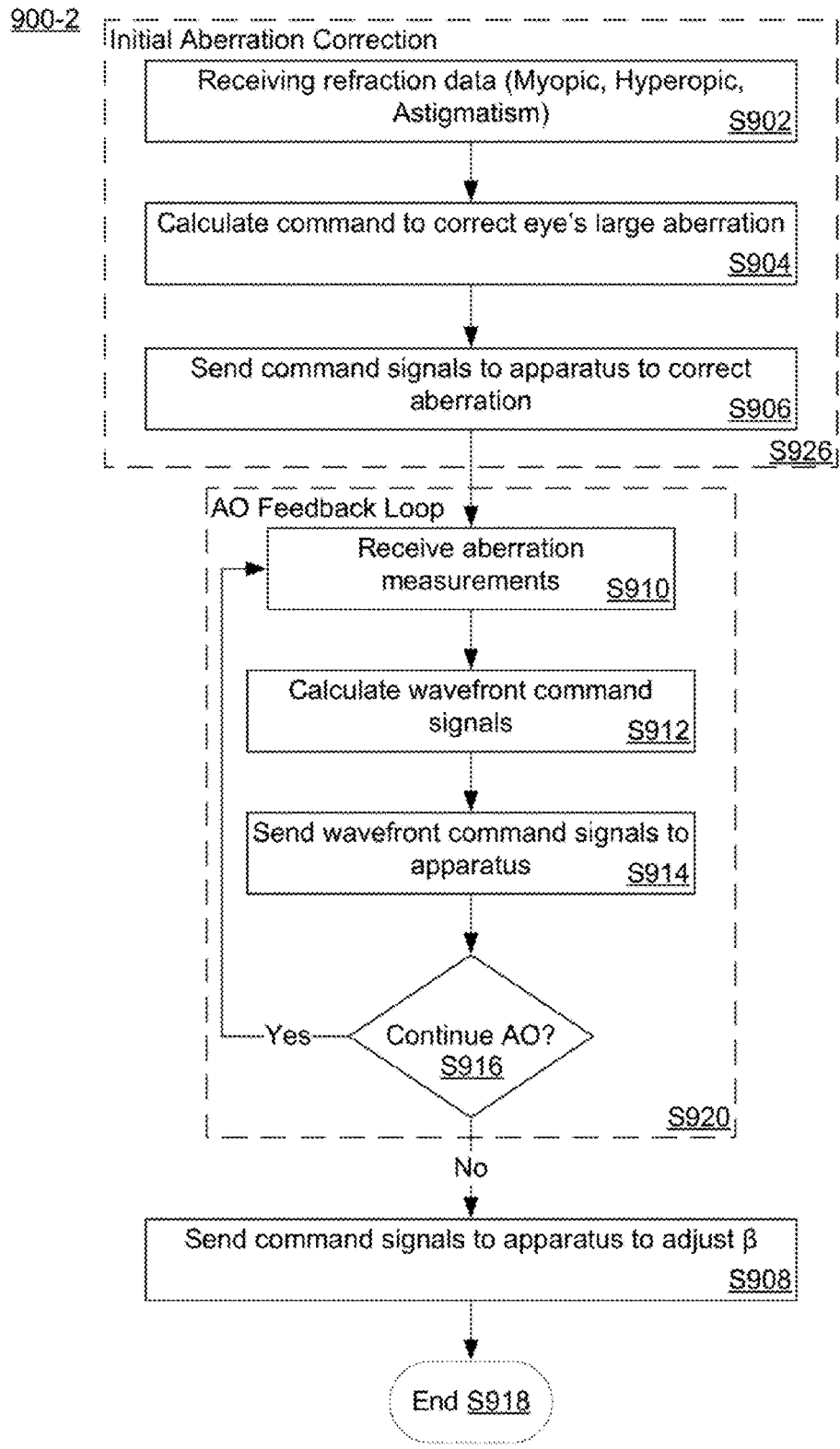

FIG. 9B is an illustration of another method 900-2 that is substantially similar to method 900-1 except the step S908 is performed after step S916. In an alternative embodiment the controller adjusts β both before and after the AO feedback loop S920. The steps S902, S904, and S906 may be combined into a single sub-method S926.

A Third Setup Method

Figure 9C:
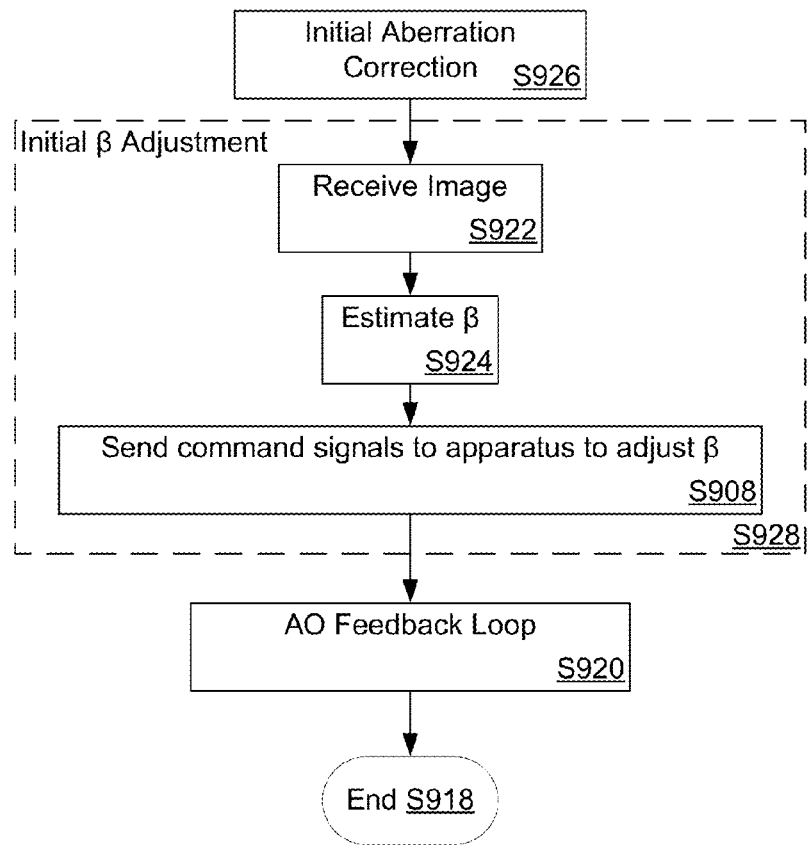

FIG. 9C is an illustration of a third method 900-3 that is substantially similar to method 900-1. The third method 900-3 includes an image receiving step S922 of the controller 116 obtaining a first test image of the subject 111 from the apparatus 100. The first test image may be an OCT image, anterior image, a SLO image, or any image which may be analyzed by the controller to determine a tilt α of the area of the subject being imaged.

The third method 900-3 may include a step S924 in which the controller 116 estimates a β to compensate for the tilt α and improve the images obtained by the apparatus 100. The third method 900-3 may then go on to complete the steps S908 and S920 described in the previous methods 900-1 and 900-2.

An alternative embodiment may include repeating steps S922, S924, and S908 until a particular criteria is met. The particular criteria may be a threshold for the tilt α as measured in the images obtained in step S922. The particular criteria may include one or more quality metrics of the image obtained in step S922. The steps S922, S924, and S908 may be combined into a sub-method S928. The order of the steps in sub-method S928 may be rearranged.

A Fourth Setup Method

Figure 9D:
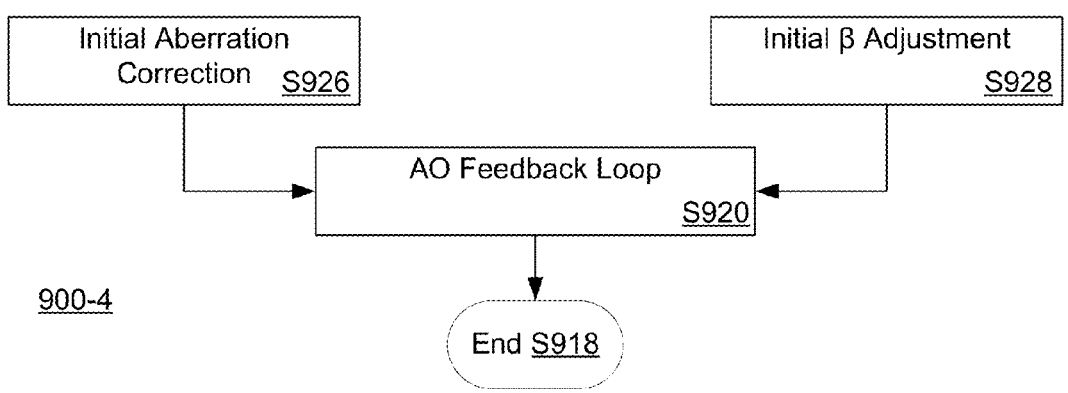

FIG. 9D is an illustration of a fourth method 900-4 that is substantially similar to method 900-3. In the fourth method 900-4, the first test image may be a stored image which may be obtained from the subject 111 prior to setting up the apparatus 100. In which case, the initial aberration correction sub-method S926 and the initial β adjustment sub-method S928 may be performed independently of each other as illustrated in FIG. 9D. The first test image may be supplied by an operator, retrieved from a database, retrieved from local storage, or retrieved from a networked storage device. After the sub-methods S926 and S928 are performed the AO feedback loop S920 may be performed.

A Fifth Setup Method

Figure 9E:
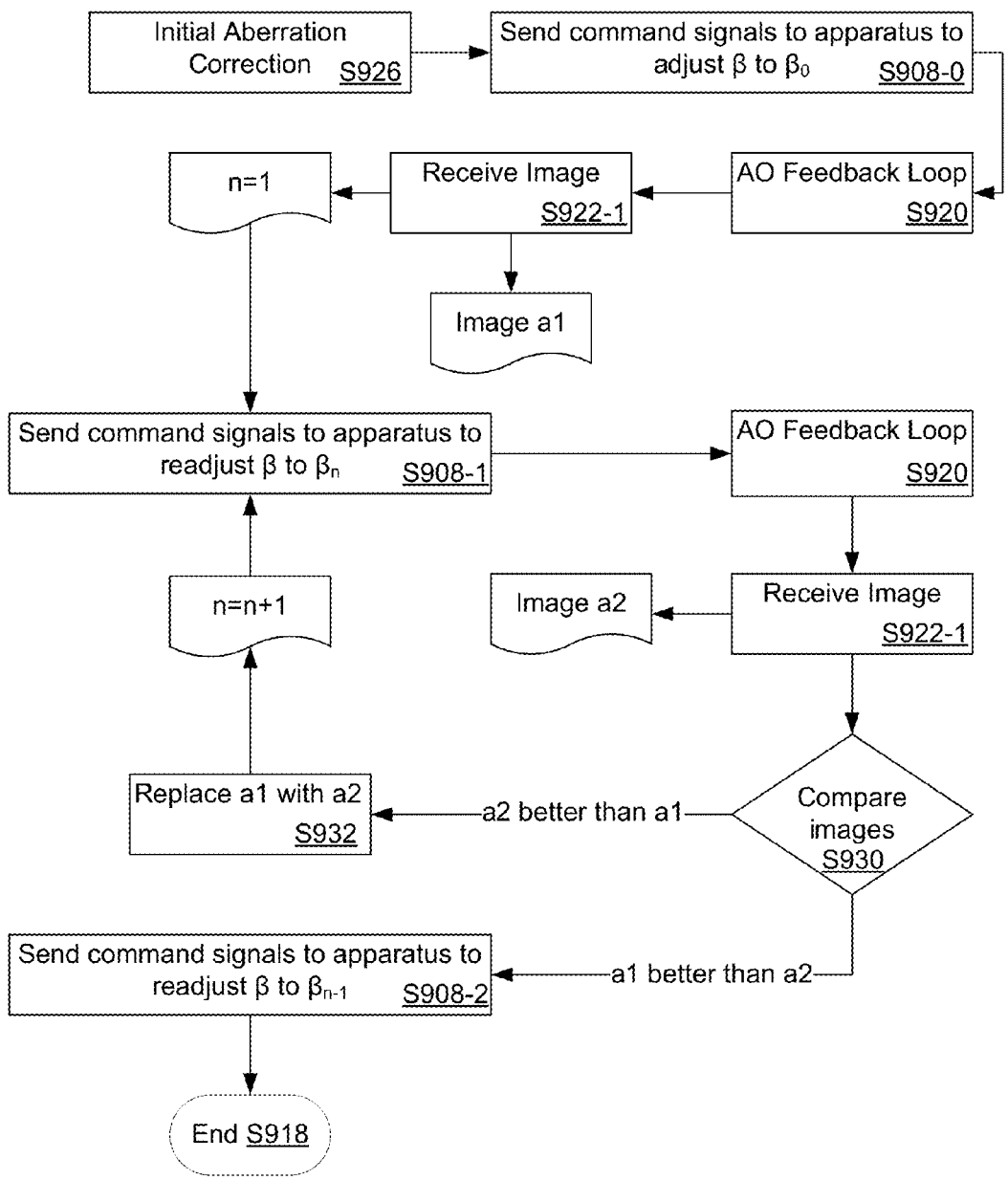

FIG. 9E is an illustration of a fifth method 900-5 that is substantially similar to method 900-3. The fifth method 900-5 may start with the sub-method S926 described above in which the initial aberration is corrected. The controller 116 may then perform step S908-0 in which the controller 116 may send instructions to the apparatus 100 adjust β to an initial value $β_0$. This initial adjustment of β may be done based on previously obtained information or may be skipped. The adjustment of β may also vary depending on the imaging location.

After β is adjusted an AO feedback loop S920 may be performed by the controller 116. The controller 116 may then receive an image a1 of the subject 111 in a step S992-1 that is substantially similar to step S922 discussed above. The image a1 may be a SLO image, an AO-SLO image, or an OCT image. The image a1 may be any image that can be analyzed by the controller 116 to provide information that can be used to obtain a quality metric that is indicative of the quality of the information which will be provided by future images of the subject 111. Also an index n may be set to 1.

After the image a1 is obtained, the controller 116 may send instructions to the apparatus to readjust β in a step S908-1 to a new $β_n$. The new value of $β_n$ may be based on information obtained from previous images of the subject 111 such as image a1. The new value of $β_n$ may be a test value for β that is not based on previous images of the subject 111.

The controller 116 may then perform the AO feedback loop sub-method S920. In the sub-method S920 the controller receives information about the state of the wavefront and then sends commands to the apparatus to change the state of the wavefront until the state of the wavefront meets a specific set of criteria.

The controller 116 may then receive a new image a2 from the apparatus 100 in a repeat of step S922-1. The controller 116 may then compare image a1 to image a2 in a step S930. The controller 116 may calculate one or more quality metrics of images a1 and a2. Examples of quality metrics are: average brightness; average sharpness, intensity uniformity, sharpness of a feature of interest; etc. A quality metric may be a quantitative value or values that give at least a probabilistic indication of the quality of the images and the ability to identify information that is of diagnostic interest in the image. The controller 116 may then choose which of images a1 or a2 is the better image as indicated by the quality metrics.

If the controller 116 determines that image a2 is better than image a1 then the method 900-5 moves on to step S932 in which image a1 is replaced with image a2. The index n is also incremented. After which steps S908-1, S920, S922-1, and S930 are repeated. These steps may be repeated a set number of times or until one or more of the quality metrics for image a2 is above a quality metric threshold.

If the previous image a1 is better than image a2 as represented by the quality metrics then the method 900-5 moves on to step S908-2. In which case, the offset β is reset to the pervious offset $β_{n-1}$. The method 900-5 may then end in a step S918. The method 900-5 describes a method of adjusting β from an initial value $β_0$ to a new value in a single direction. This method may also be adapted to adjust β in multiple directions and on multiple scales. The offset β may also be a vector in which case peak/valley seeking method may be used to optimize β. The method 900-5 may also be stopped when the index n reaches a set value.

An imaging Method

Figure 10:
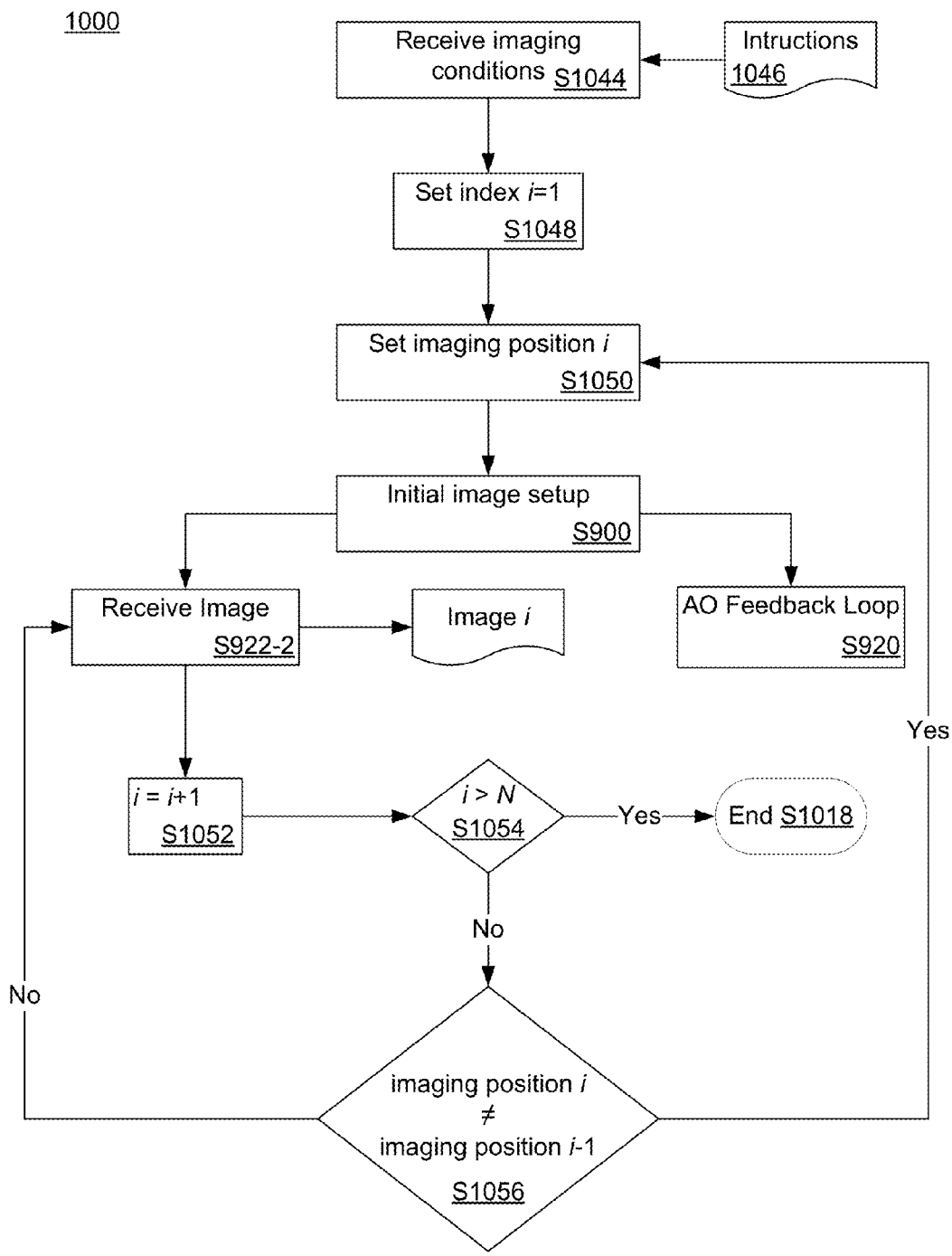
FIG. 10 is an illustration of a method performed by embodiments.

FIG. 10 is an illustration of an imaging method 1000. Imaging method 1000 may include a first step S1044 of the controller 116 receiving a first set of imaging instructions 1046. The first set of imaging instructions 1046 may be a default set of instructions, instructions received from an operator, instructions stored on the controller 116, instructions received over a network, instructions received from a database, a combination of these sources or some other source. The first set of imaging instructions may include instructions for obtaining N images. N is an integer 1 or larger. These N images may be stitched together to obtain a panoramic image, aligned and averaged together to obtain a lower noise image, and/or used to obtain a time series video of the imaging area. The first set of imaging instructions may include parameters, such as size and position for each imaging area i, wherein i is an integer index between 1 and N.

After receiving the imaging conditions, the controller 116 may set an index i to 1 in a step S1048. The controller 116 may then, in a step S1050, send instructions to the imaging apparatus 100 to set the imaging position so as to obtain an image i. The controller 116 may then initiate a sub-method 900. Several examples of possible implementations of sub-method 900 were described above as methods 900-1, 900-2, 900-3, 900-4, and 900-5. In the sub-method 900, the controller 116 may send instructions to the apparatus 100 to compensate for known aberrations and to adjust the offset β so as to optimize the imaging of the subject.

After an appropriate β has been set for an imaging position i the AO feedback loop may be started and run continuously while a new image i for imaging position i is obtained. The controller may then receive a new image i for imaging position i in a step S922-2. Alternatively, one of the images obtained during sub-method S900 may be used as image i.

After image i is obtained, the index i may be incremented in a step S1052 by the controller 116. The controller 116 may then check the index i against the limit N to determine if all of the images have been obtained in a step S1054. If all of the images have been obtained then controller 116 may stop the method in a step S1018; the AO feedback loop S920 may also be stopped at this time. If the index i has not reached the limit N and there are more images to obtain then the controller 116 may go onto to testing step S1056.

In the step S1056, the controller 116 may check if the imaging position needs to be changed to obtain new image i after i has been incremented. If the imaging position does not change then the controller 116, may move on to step S922-2 and receive a new image; AO feedback loop continues to run during this process. This will follow a loop until all N images are obtained. If the imaging position does change then controller 116 will move back to step S1050; the AO feedback loop may be temporarily stopped at this point; followed by sub-method S900 and so on. Some steps in sub-method S900 may be skipped if this is not the first time S900 is run. For examples sub-method S926 may be skipped.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A method for imaging a fundus of a subject comprising:
   obtaining an image of the fundus of the subject from an ophthalmoscope;
   obtaining an image quality of the image of the fundus of the subject;
   estimating a first illumination center position for an illumination beam relative to a center position of a pupil of the subject based on the image quality;
   wherein, the first illumination center position is offset from the center position of the pupil; and
   sending instructions to the ophthalmoscope to shift a center position of the illumination beam to the first illumination center position.

2. The method of claim 1, wherein shifting the center position of the illumination beam to the first illumination center position and away from the center of the pupil, improves the image quality of the image of the fundus obtained by the ophthalmoscope.

3. The method of claim 2, wherein the image quality of the image of the fundus is estimated based on one or more properties of the image of the fundus including: a contrast ratio; a brightness, and a spatial frequency.

4. The method of claim 1, wherein estimation of the first illumination center position is based on one or more images selected from:
   an OCT image;
   an anterior ocular segment image;
   a SLO image;
   a first image that includes information about a surface tilt of a surface of an area of the fundus being imaged; and
   a second image that includes information about a sub-surface tilt of a sub-surface feature below the area of the fundus being imaged.

5. The method of claim 1, further comprising:
   displaying results of an aberration measurement along with direction and magnitude the first illumination center position relative to the center of the pupil.

6. The method of claim 1, wherein the ophthalmoscope is an adaptive optics scanning laser ophthalmoscope having an aberration measurement optical system to measure aberration of the subject and obtain fundus images.

7. The method of claim 1, wherein the ophthalmoscope shifts the center position, with one or more of: a movable mirror, a movable lens, a moveable window, and a phase shifter.

8. The method of claim 1, wherein the ophthalmoscope maintains the center position of the illumination beam at the first illumination center position offset from the center position of the pupil during scanning, wherein during scanning the illumination beam is scanned across an area of the fundus.

9. The method of claim 1, wherein shifting the center position of the illumination beam reduces the amount of light which is incident on the fundus and increases the image quality of the image of the fundus.

10. The method of claim 1, wherein estimating the first illumination center position further comprises:
sending instructions to the ophthalmoscope to shift the center position of the illumination beam to a test illumination center position;
obtaining a test image from the ophthalmoscope;
obtaining a quality metric based on the test image;
comparing the quality metric to a first threshold;
in the case where the quality metric does not meet the first threshold performing a first sub-test method comprising:
sending instructions to the ophthalmoscope to shift the center position of the illumination beam to a new test illumination center position;
obtaining a new test image from the ophthalmoscope;
obtaining a new quality metric based on the new test image;
comparing the new quality metric to the first threshold;
in the case where the new quality metric does meet the first threshold setting the new test illumination center position as the first illumination center position;
in the case where the new quality metric does not meet the first threshold repeating the first sub-test method with a different new test illumination center position; and
in the case where the quality metric does meet the first threshold, setting the test illumination center position as the first illumination center position.

11. A method for imaging a fundus of a subject comprising:
estimating a first illumination center position for an illumination beam relative to a center position of a pupil of the subject, wherein the first illumination center position is offset from the center position of the pupil; and
sending instruction to an ophthalmoscope to shift a center position of the illumination beam to the first illumination center position,
wherein the estimation of the first illumination center position comprises:
identifying an interface of a feature on or below an area of the fundus being imaged;
estimating a tilt of the interface;
estimating a first incidence angle at which the illumination beam irradiates the interface so as to minimize how much light reflected by the interface with the tilt is blocked by the pupil;
estimating the first illumination center position such that the illumination beam is incident on the area of the fundus being imaged at the first incidence angle based on optical properties of the subject.

12. The method of claim 11, wherein the optical properties of the subject are estimated based on an eyeglass prescription of the subject.

13. The method of claim 11, wherein the interface is a line between the photoreceptor interior segment and the photoreceptor outer segment measured within an OCT image.

14. A method for imaging a fundus of a subject comprising:
estimating a first illumination center position for an illumination beam relative to a center position of a pupil of the subject, wherein, the first illumination center position is offset from the center position of the pupil; and
sending instructions to an ophthalmoscope to shift a center position of the illumination beam to the first illumination center position,
wherein:
imaging the fundus comprises obtaining a plurality of images;
each image among the plurality of images is representative of a particular area of the fundus;
each particular area of the fundus is associated with a particular first illumination center position; and
each image received from the ophthalmoscope is obtained with the center position of the illumination beam shifted to the particular first illumination center position associated with the particular area of the fundus being imaged.

15. The method of claim 14, wherein each of the particular first illumination centers is stored as a plurality of first illumination centers, each of the plurality of first illumination centers is associated with a particular area of the subject.

16. A non-transitory computer-readable medium encoded with instructions for performing a method for imaging a fundus of a subject comprising:
instructions for obtaining an image of the fundus of the subject from an ophthalmoscope;
instructions for obtaining an image quality of the image of the fundus of the subject;
instructions for estimating a first illumination center position for an illumination beam relative to a center position of a pupil of the subject based on the image quality;
wherein, the first illumination center position is offset from the center position of the pupil; and
instructions for sending instructions to the ophthalmoscope to shift a center position of the illumination beam to the first illumination center position.

17. A controller configured to control an ophthalmoscope for imaging a fundus of a subject comprising:
a processor; and
a memory;
wherein the processor obtains an image of the fundus of the subject from an ophthalmoscope;
wherein the processor obtains an image quality of the image of the fundus of the subject;
wherein the processor estimates a first illumination center position for an illumination beam relative to a center position of a pupil of the subject based on the image quality;
wherein, the first illumination center position is offset from the center position of the pupil; and
wherein the processor sends instructions to the ophthalmoscope to shift a center position of the illumination beam to the first illumination center position.

18. The controller according to claim 17 further comprising the ophthalmoscope.

19. The controller according to claim 18 further comprising an optical component configured to shift the center position of the illumination beam to the first illumination center position.

* * * * *